United States Patent
Wang et al.

(12)

(10) Patent No.: US 11,208,494 B2
(45) Date of Patent: Dec. 28, 2021

(54) MONOCLONAL ANTIBODIES SPECIFIC TO THE PLEXIN-SEMAPHORIN-INTEGRIN (PSI) DOMAIN OF RON FOR DRUG DELIVERY AND ITS APPLICATION IN CANCER THERAPY

(71) Applicant: PCM TARGETECH, LLC, Amarillo, TX (US)

(72) Inventors: Ming-Hai Wang, Plano, TX (US); Hang-Ping Yao, Amarillo, TX (US)

(73) Assignee: PCM TARGETECH, LLC, Amarillo, TX (US)

( * ) Notice: Subject to any disclaimer, the term of this patent is extended or adjusted under 35 U.S.C. 154(b) by 0 days.

(21) Appl. No.: 16/529,205

(22) Filed: Aug. 1, 2019

(65) Prior Publication Data

US 2019/0352422 A1 Nov. 21, 2019

Related U.S. Application Data

(63) Continuation of application No. PCT/US2017/050448, filed on Sep. 7, 2017.

(60) Provisional application No. 62/384,989, filed on Sep. 8, 2016.

(51) Int. Cl.
*C07K 16/28* (2006.01)
*A61K 47/68* (2017.01)

(52) U.S. Cl.
CPC ...... *C07K 16/2896* (2013.01); *A61K 47/6803* (2017.08); *A61K 47/6849* (2017.08); *C07K 2317/20* (2013.01); *C07K 2317/21* (2013.01); *C07K 2317/24* (2013.01); *C07K 2317/565* (2013.01); *C07K 2317/567* (2013.01); *C07K 2317/73* (2013.01); *C07K 2317/77* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 8,133,489 B2 | 3/2012 | Pereira et al. |
| 2009/0226442 A1 | 9/2009 | Huet et al. |
| 2009/0246205 A1 | 10/2009 | Pereira et al. |
| 2012/0027773 A1 | 2/2012 | Whalen et al. |

OTHER PUBLICATIONS

Zarei et al. (J. Cancer Res. Clin. Oncology Aug. 8, 2016) (Year: 2016).*
Almagro & Fransson, Frontiers in Bioscience 2008; 13:1619-33 (Year: 2008).*
International search report of PCT Patent Application No. PCT/US2017/050448 dated Jan. 11, 2018.
Jennifer M. O'Toole et al., Therapeutic Implications of a Human Neutralizing Antibody to the Macrophage-Stimulating Protein Receptor Tyrosine Kinase (RON), a c-MET Family Member, Cancer Research, Sep. 15, 2006, pp. 9162-9170, vol. 66, Issue 18.
Kohler G. et al., Continuous Cultures of Fused Cells Secreting Antibody of Predefined Specificity, Nature, Aug. 7, 1975, pp. 495-497, vol. 256.

\* cited by examiner

*Primary Examiner* — Peter J Reddig

(57) ABSTRACT

The present invention includes unique, isolated monoclonal antibodies that bind the PSI domain of human RON ($RON^{PSI}$), and methods for making and using the same and novel combination therapies of anti-$RON^{PSI}$ antibodies, including humanized anti-$RON^{PSI}$ antibodies, nucleic acids that encode the heavy chain, the light chain, or both the light and heave chains of the antibody, host cells, expression vectors, and wherein the antibody or binding fragments thereof can be further conjugated with one or more cytotoxic or chemotherapeutic agents.

8 Claims, 6 Drawing Sheets

Specification includes a Sequence Listing.

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
ggctacacct tcacagacta tcacatggat                               30

<210> SEQ ID NO 2
<211> LENGTH: 51
<212> TYPE: DNA
<213> ORGANISM: Artificial Sequence
<220> FEATURE:
<223> OTHER INFORMATION: Synthetic primer

<400> SEQUENCE: 2
gacatcaacc caaacaatgg cggcgccatc tacaatcaga gtttaaggg c         51

<210> SEQ ID NO 3
<211> LENGTH: 39
<212> TYPE: DNA
<213> ORGANISM: Artificial Sequence
<220> FEATURE:
<223> OTHER INFORMATION: Synthetic primer

<400> SEQUENCE: 3
tctcactacg attatgctgg aggagcttgg ttcgcttac                     39

<210> SEQ ID NO 4
<211> LENGTH: 51
<212> TYPE: DNA
<213> ORGANISM: Artificial Sequence
<220> FEATURE:
<223> OTHER INFORMATION: Synthetic primer

<400> SEQUENCE: 4
aagagctccc agagcctgct gttctccggc aaccagaaga attacctggc t        51

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
tgggcttcta ccagagctag c                                        21

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
cagcagtact atagcttccc aagaacc                                  27

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Gly Tyr Thr Phe Thr Asp Tyr His Met Asp
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Asp Ile Asn Pro Asn Asn Gly Gly Ala Ile Tyr Asn Gln Lys Phe Lys
1               5                   10                  15

Gly

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Ser His Tyr Asp Tyr Ala Gly Gly Ala Trp Phe Ala Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Lys Ser Ser Gln Ser Leu Leu Phe Ser Gly Asn Gln Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Trp Ala Ser Thr Arg Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Gln Gln Tyr Tyr Ser Phe Pro Arg Thr
1               5

<210> SEQ ID NO 13

```
<211> LENGTH: 1425
<212> TYPE: DNA
<213> ORGANISM: Homo sapiens

<400> SEQUENCE: 13
gccgccacca tggggttggtc atgtattatt ctgtttctgg tggctactgc taccggcgtg      60
cattcccagg tgcagctggt ccagtctggg gctgaagtga agaagcccgg cgccaccgtg     120
aagatcagct gcaaggtgtc cggctacacc ttcacagact atcacatgga ttgggtgcag     180
caggctcctg gcaagggcct cgagtggatg ggcgacatca acccaaacaa tggcggcgcc     240
atctacaatc agaagtttaa gggccgggtg accatcacag ctgacacctc tacagatacc     300
gcctatatgg agctgagctc cctgagatcc gaggacacag ccgtgtacta ttgcgcccgg     360
tctcactacg attatgctgg aggagcttgg ttcgcttact ggggacaggg cacactggtg     420
accgtgagcc gggcttccac caagggccct agcgtgtttc cactggcccc ctcttccaag     480
tctacaagcg gaggaaccgc cgctctggga tgtctggtga aggattactt cccagagccc     540
gtgaccgtgt cttggaacag cggcgctctg acaagcggcg tgcacacatt tcctgccgtg     600
ctgcagtcct ctggcctgta ctccctgagc tccgtggtga cagtgccatc tagctccctg     660
ggcacacaga cctatatctg caacgtgaat cacaagccaa gcaataccaa ggtggacaag     720
aaggtggagc ccaagtcctg tgataagaca cacacctgcc cccccttgtcc tgctccagag     780 ctgctgggag accttccgt gttcctgttt ccacccaaac ctaaggacac actgatgatc     840
tctcggacac cagaggtgac ctgcgtggtg gtggacgtga gccacgagga tcccgaggtg     900
aagttcaact ggtatgtcga tggcgtggag gtgcacaatg ccaagaccaa gccccggggag     960 gagcagtaca actctacata tagggtggtg agcgtgctga ccgtgctgca ccaggactgg    1020
ctcaacggca aggagtataa gtgcaaggtg tccaataagg ctctgccgc ccctatcgag    1080 aagacaatct ctaaggctaa gggccagcct agggagccac aggtgtacac cctgcctcca    1140
tctagagacg agctgacaaa gaaccaggtg agcctgacct gtctggtgaa gggcttctat    1200
cccagcgata tcgccgtgga gtgggagtcc aatggccagc ctgagaacaa ttacaagacc    1260
acaccccctg tgctggactc cgatggctct ttctttctgt attccaagct gaccgtggat    1320
aagtctcggt ggcagcaggg caacgtgttc agctgttctg tgatgcacga agccctgcat    1380
aatcactata cccagaaatc cctgagtctg tcacctggaa agtga                    1425

<210> SEQ ID NO 14
<211> LENGTH: 729
<212> TYPE: DNA
<213> ORGANISM: Homo sapiens

<400> SEQUENCE: 14
gccgccacca tgggctggtc atgtattatt ctgtttctgg tcgcaactgc tactggggtg      60
catagcgaaa tcgtgatgac tcagtctccc ggaaccctgt ccctgtctcc aggcgagcgg     120
gccaccctgt cctgcaagag ctcccagagc ctgctgttct ccggcaacca gaagaattac     180
ctggcttggt atcagcagaa gccaggccag gctcccaggc tgctgatcta ctgggcttct     240
accgagctga gcggcatccc cgacaggttc agcggctccg gctctggcac agacttcacc     300
ctgacaatct ctagactgga gcctgaggac ttcgccgtgt actattgcca gcagtactat     360
agcttcccaa gaacctttgg ccagggcaca aagctggaga tcaagcggac cgtggccgct     420
cccagcgtgt tcatcttccc ccttccgac gagcagctga gtccggcac agcttctgtg     480 gtgtgcctgc tgaacaactt ctaccccagg gaggccaagg tccagtggaa ggtggataac     540
```

```
gctctgcaga gcggcaattc ccaggagtct gtgaccgagc aggacagcaa ggattccaca      600
tattctctgt ctagcaccct gacactgtct aaggccgatt acgagaagca aaggtgtat      660 gcttgtgaag tcacccacca gggtctgtca tcacccgtca ctaagtcttt taaccgaggc      720
gaatgctga                                                              729
```

```
<210> SEQ ID NO 15
<211> LENGTH: 471
<212> TYPE: PRT
<213> ORGANISM: Homo sapiens

<400> SEQUENCE: 15
```

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Thr Val Lys Ile Ser Cys Lys Val Ser Gly Tyr Thr Phe
        35                  40                  45

Thr Asp Tyr His Met Asp Trp Val Gln Gln Ala Pro Gly Lys Gly Leu
    50                  55                  60

Glu Trp Met Gly Asp Ile Asn Pro Asn Asn Gly Ala Ile Tyr Asn
65                  70                  75                  80

Gln Lys Phe Lys Gly Arg Val Thr Ile Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Ser His Tyr Asp Tyr Ala Gly Gly Ala Trp Phe
        115                 120                 125

Ala Tyr Trp Gly Gln Gly Thr Leu Val Thr Val Ser Arg Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 16
<211> LENGTH: 239
<212> TYPE: PRT
<213> ORGANISM: Homo sapiens

<400> SEQUENCE: 16

Met Gly Trp Ser Cys Ile Ile Leu Phe Leu Val Ala Thr Ala Thr Gly
1               5                   10                  15

Val His Ser Glu Ile Val Met Thr Gln Ser Pro Gly Thr Leu Ser Leu
            20                  25                  30

Ser Pro Gly Glu Arg Ala Thr Leu Ser Cys Lys Ser Ser Gln Ser Leu
            35                  40                  45

Leu Phe Ser Gly Asn Gln Lys Asn Tyr Leu Ala Trp Tyr Gln Gln Lys
        50                  55                  60

Pro Gly Gln Ala Pro Arg Leu Leu Ile Tyr Trp Ala Ser Thr Arg Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Tyr Ser Phe Pro Arg Thr Phe Gly Gln Gly Thr Lys
            115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys

```
<210> SEQ ID NO 17
<211> LENGTH: 54
<212> TYPE: PRT
<213> ORGANISM: Homo sapiens

<400> SEQUENCE: 17

Pro Ile Arg Gly Pro Gly Cys Arg His Phe Leu Thr Cys Gly Arg Cys
1               5                   10                  15

Leu Arg Ala Trp His Phe Met Gly Cys Gly Trp Cys Gly Asn Met Cys
            20                  25                  30

Gly Gln Gln Lys Glu Cys Pro Gly Ser Trp Gln Gln Asp His Cys Pro
        35                  40                  45

Pro Lys Leu Thr Glu Phe
    50
```

MONOCLONAL ANTIBODIES SPECIFIC TO THE PLEXIN-SEMAPHORIN-INTEGRIN (PSI) DOMAIN OF RON FOR DRUG DELIVERY AND ITS APPLICATION IN CANCER THERAPY

CROSS-REFERENCE TO RELATED APPLICATION

The present application is a Continuation Application of PCT Application No. PCT/US2017/050448 filed on Sep. 7, 2017, which claims the benefit of U.S. Provisional Application No. 62/384,989 filed on Sep. 8, 2016. The contents of the above are hereby incorporated by reference in their entirety.

REFERENCE TO SEQUENCE LISTING

The substitute sequence listing is submitted to replace the previously submitted sequence listing as an ASCII formatted text filed via EFS-Web, with a file name of "Substitute Sequence Listing ZZZHCH-19003-USPT.TXT", a creation date of Apr. 18, 2021, and a size of 12,626 bytes. The substitute sequence Listing filed via EFS-Web is part of the specification and is incorporated in its entirety by reference herein.

TECHNICAL FIELD OF THE INVENTION

The present invention relates in general to the field of monoclonal antibodies, and more particularly, to anti-recepteur d'origine nantais (RON) monoclonal antibodies specific to the Plexin-Semaphorin-Integrin (PSI) domain of RON for drug delivery and its application in cancer therapy.

BACKGROUND OF INVENTION

Without limiting the scope of the invention, its background is described in connection with RON (recepteur d'origine nantais).

The pathogenic roles of RON in cancer biology have been extensively studied under various genetic, biochemical, and biological models. Evidence from both in vitro and in vivo pre-clinical experiments has revealed that RON signaling is involved in cellular growth and invasiveness in different types of epithelial cancers. Aberrant RON expression is characterized by protein overexpression and generation of oncogenic variants, e.g., in cancers derived from stomach, colon, breast, prostate, lung, and pancreatic tissues.

The RON receptor is a tyrosine kinase. Various types of cancers, e.g., breast, colon, lung, and pancreatic, display aberrant RON expression including overexpression, isoform generation, and constitutive activation. Specific antibodies bind to RON on the surface of cancerous cells and cause RON internalization.

U.S. Pat. No. 8,133,489, issued to Pereira, et al., entitled "Inhibition of macrophage-stimulating protein receptor (RON) and methods of treatment thereof." Briefly, the disclosure is directed to antibodies or fragments thereof, including human antibodies, specific for Macrophage-Stimulating Protein Receptor (MSP-R or RON), which inhibited RON activation. Also provided are methods to inhibit RON, particularly the use of RON antibodies to treat diseases such as cancer.

Pereira, D. S., et al., have also published about the "Therapeutic implications of a human neutralizing antibody to the macrophage-stimulating protein receptor tyrosine kinase (RON), a c-MET family member", Cancer Research, Volume 66, issue 18, 15 Sep. 2006, Pages 9162-9170. This publication discusses anti-RON antibodies in vivo efficacy against tumor xerographs, in which anti-RON antibodies were made through phage display.

U.S. Patent Application Publication No. 2009/0246205, entitled, "Inhibition of macrophage-stimulating protein receptor (RON)", which was directed to methods for treatment of tumors and other diseases in a mammal comprising administration of antibodies specific for Macrophage-Stimulating Protein Receptor ("MSP-R" or "RON"). Compositions comprising antibodies or antibody fragments specific for RON, including human antibodies, that inhibit RON activation are also said to be disclosed.

U.S. Patent Application Publication No. 2012/0027773, entitled Anti-RON antibodies, which is said to teach monoclonal antibodies that bind and inhibit activation of human RON (Recepteur d'Origine Nantais). The antibodies area said to be useful for treating certain forms of cancer that are associated with activation of RON.

Finally, U.S. Patent Application Publication No. 2009/0226442 is entitled, "RON antibodies and uses thereof", and is said to teach antibodies that bind to RON (MST1R), and uses thereof. In particular in the diagnosis and treatment of cancer, the antibodies inhibit RON-mediated pro-survival and tumor proliferation pathways, and variants, fragments, and derivatives thereof. Also taught are antibodies that block the ability of the ligand, MSP to bind to RON, as well as fragments, variants and derivatives of such antibodies. The invention also includes polynucleotides encoding the above antibodies or fragments, variants or derivatives thereof, as well as vectors and host cells comprising such polynucleotides. The invention further includes methods of diagnosing and treating cancer using the antibodies of the invention.

Although antibodies that bind RON are known in the art, there is still a need for improved RON antibodies that can be used as therapeutic agents.

SUMMARY OF THE INVENTION

In one embodiment, the present invention includes an isolated monoclonal antibody or binding fragment thereof that specifically binds a Plexin-Semaphorin-Integrin (PSI) domain of human RON, comprising a monoclonal antibody selected from H5B14 or PCM5B14. In one aspect, the monoclonal antibody or binding fragment thereof comprises complementarity determining region (CDR) sequences interposed between human or humanized framework sequences, wherein the immunoglobulin heavy chain variable region comprises a CDRH1; a CDRH2; and a CDRH3 for a monoclonal antibody selected from SEQ ID NOS:7, 8, and 9, respectively or conservative substitutions thereof and an immunoglobulin light chain variable region that comprises: a CDRL1; a CDR L2; and a CDR L3 for a monoclonal antibody selected from SEQ ID NOS:10, 11, and 12, respectively or conservative substitutions thereof. In another aspect, the monoclonal antibody or binding fragment thereof is combined with a cytotoxic agent, such that the antibody targets a RON protein on a cell and the RON-monoclonal antibody and the cytotoxic agent are internalized into the cell. In another aspect, the antibody or binding fragment thereof are a fusion protein with a cytotoxic protein. In another aspect, the antibody or binding fragment further comprises a cytotoxic or chemotherapeutic agent that is conjugated to the antibody or binding fragment thereof. In another aspect, the humanized antibody is expressed from nucleic acids SEQ ID NOS: 13 and 14, into amino acid sequences SEQ ID NOS:15 and 16.

Another embodiment of the present invention includes a method of making an antibody or binding fragment thereof that specifically binds a PSI domain of human RON in a host cell, the method comprising: expressing an immunoglobulin heavy chain variable region or an immunoglobulin light chain variable region, or both, that specifically binds a Plexin-Semaphorin-Integrin (PSI) domain of human RON under conditions in which the host cell expresses a polypeptide comprising the immunoglobulin heavy chain variable region, the immunoglobulin light chain variable region, or both, thereby producing the antibody or the binding fragment thereof selected from an H5B14 or a PCM5B14 antibody; and purifying the antibody or the binding fragment thereof. In one aspect, the host cell is an H5B1.4 or PCM5B14 hybridoma cell. In another aspect, the method further comprises the step of conjugating a cytotoxic or chemotherapeutic agent to the antibody or binding fragment thereof, or making a fusion protein with a cytotoxic protein. In another aspect, the host cell is selected from a bacterial, yeast, insect, plant, or mammalian cell. In another aspect, the cancer is selected from brain, breast, cervix, pancreatic, skin, prostate, liver, bladder, colon, head & neck, kidney, lung, non-small cell lung, melanoma, mesothelioma, ovary, sarcoma, stomach, uterus and medulloblastoma. In another aspect, the humanized antibody is expressed from nucleic acids SEQ ID NOS: 13 and 14, into amino acid sequences SEQ ID NOS:15 and 16.

Another embodiment of the present invention includes an isolated polypeptide or binding fragment thereof that specifically binds a PSI domain of human RON, comprising an immunoglobulin heavy chain variable region and/or an immunoglobulin light chain variable region having at least a 95, 96, 97, 98, 99, or 100% homology to the amino acid sequences selected from the group consisting of the Heavy chains and Light chains of a monoclonal antibody that expresses the complementarity determining regions (CDRs) from H5B14 or PCM5B14. In another aspect, the immunoglobulin heavy chain variable region that comprises a CDRH1; a CDRH2; and a CDRH3 for a monoclonal antibody selected from SEQ ID NOS:7, 8, and 9, respectively; and an immunoglobulin light chain variable region that comprises: a CDRL1; a CDR L2; and a CDR L3 for a monoclonal antibody selected from SEQ ID NOS:10, 11, and 12, respectively. In another aspect, the CDR sequences are interposed between human and humanized framework sequences. In another aspect, the humanized antibody is expressed from nucleic acids SEQ ID NOS: 13 and 14, into amino acid sequences SEQ ID NOS:15 and 16.

Yet another embodiment of the present invention includes a method of inhibiting or reducing proliferation of a tumor cell comprising exposing the cell to an isolated monoclonal antibody or binding fragment thereof that specifically binds human a Plexin-Semaphorin-Integrin (PSI) domain of RON from monoclonal antibody H5B14 or PCM5B14 attached to a cytotoxic agent, in an amount effective to inhibit or reduce proliferation of the tumor cell. In another aspect, the tumor cell is in a mammal or a human. In another aspect, the humanized antibody is expressed from nucleic acids SEQ ID NOS: 13 and 14, into amino acid sequences SEQ ID NOS:15 and 16.

Another embodiment of the present invention includes an isolated antibody or binding fragment thereof that binds the PSI domain of human RON, comprising an immunoglobulin heavy chain variable region and/or an immunoglobulin light chain variable region having at least a 95% homology of the monoclonal antibody of H5B14 or PCM5B14. In one aspect, the immunoglobulin heavy chain variable region comprises: a $CDR_{H1}$ comprising an amino acid sequence of SEQ ID NO:7; a $CDR_{H2}$ comprising an amino acid sequence of SEQ ID NO:8; and a $CDR_{H3}$ comprising an amino acid sequence of SEQ ID NO:9. In another aspect, the immunoglobulin light chain variable region comprises: a $CDR_{L1}$ comprising an amino acid sequence of SEQ ID NO:10; a $CDR_{L2}$ comprising an amino acid sequence of SEQ ID NO:11, and a $CDR_{L3}$ comprising an amino acid sequence of SEQ ID NO:12. In another aspect, the CDR sequences are interposed between human and humanized framework sequences. In another aspect, the CDR sequences are interposed between human and humanized framework sequences further comprising a human germline framework sequence. In another aspect, the antibody pairs heavy chain CDRs selected from SEQ ID NOS: 7, 8, and 9, with light chain CDRs selected from SEQ ID NOS: 10, 11 and 12. In another aspect, the antibody is expressed from a nucleic acid that encodes the immunoglobulin heavy chain $CDR_{H1}$, $CDR_{H2}$ and $CDR_{H3}$ that are selected from SEQ ID NOS:1, 2, and 3, respectively. In another aspect, the antibody is expressed from a nucleic acid that encodes the immunoglobulin light chain $CDR_{L1}$, $CDR_{L2}$ and $CDR_{L3}$ that are selected from SEQ ID NOS: 4, 5, and 6, respectively. In another aspect, the CDR sequences are interposed between human and humanized framework sequences wherein the framework sequence comprise at least one substitution at amino acid position 27, 30, 48, 67 or 78, where in the amino acid numbering is based on Kabat. In another aspect, the humanized antibody is expressed from nucleic acids SEQ ID NOS: 13 and 14, into amino acid sequences SEQ ID NOS:15 and 16.

Another embodiment of the present invention includes an isolated nucleic acid expressing an antibody that binds the PSI domain of human RON, comprising an immunoglobulin heavy chain variable region and/or an immunoglobulin light chain variable region having at least a 95% homology of the monoclonal antibody of H5B14 or PCM5B14. In another aspect, the immunoglobulin heavy chain variable region comprises: a $CDR_{H1}$ comprising a nucleic acid sequence of SEQ ID NO:1; a $CDR_{H2}$ comprising a nucleic acid sequence of SEQ ID NO:2; and a $CDR_{H3}$ comprising a nucleic acid sequence of SEQ ID NO:3. In another aspect, the immunoglobulin light chain variable region comprises: a $CDR_{L1}$ comprising a nucleic acid sequence of SEQ ID NO:4; a $CDR_{L2}$ comprising a nucleic acid sequence of SEQ ID NO:5; and a $CDR_{L3}$ comprising a nucleic acid sequence of SEQ ID NO:6. In another aspect, the immunoglobulin heavy chain variable region and/or the immunoglobulin light chain variable region is defined further as comprising a nucleic acid sequence that encodes a cytotoxic protein and forms a fusion protein with the immunoglobulin heavy chain variable region and/or the immunoglobulin light chain variable region, or both. In another aspect, the humanized antibody is expressed from nucleic acids SEQ ID NOS: 13 and 14, into amino acid sequences SEQ ID NOS:15 and 16.

Another embodiment of the present invention includes an expression vector comprising the nucleic acid encoding an immunoglobulin heavy chain variable region and/or the immunoglobulin light chain variable region is defined further as comprising a nucleic acid sequence that encodes a cytotoxic protein and forms a fusion protein with the immunoglobulin heavy chain variable region and/or the immunoglobulin light chain variable region, or both. Another embodiment of the present invention includes a host cell comprising the expression vector comprising an immunoglobulin heavy chain variable region or an immunoglobulin light chain variable region, or both. In another aspect, the humanized antibody is expressed from nucleic acids SEQ ID NOS: 13 and 14, into amino acid sequences SEQ ID NOS:15 and 16.

Another embodiment of the present invention includes a method of producing a polypeptide comprising an immunoglobulin heavy chain variable region or an immunoglobulin light chain variable region, the method comprising: (a) growing the host cell the expresses an immunoglobulin heavy chain variable region and/or the immunoglobulin light chain variable region is defined further as comprising a nucleic acid sequence that encodes a cytotoxic protein and forms a fusion protein with the immunoglobulin heavy chain variable region and/or the immunoglobulin light chain variable region, or both, under conditions so that the host cell expresses the polypeptide comprising the immunoglobulin heavy chain variable region or the immunoglobulin light chain variable region; and (b) purifying the polypeptide comprising the immunoglobulin heavy chain variable region or the immunoglobulin light chain variable region. In another aspect, the humanized antibody is expressed from nucleic acids SEQ ID NOS: 13 and 14, into amino acid sequences SEQ ID NOS:15 and 16.

Another embodiment of the present invention includes a method of producing an antibody that binds the human RON PSI domain or an antigen binding fragment of the antibody, the method comprising: (a) growing the host cell the produces an immunoglobulin heavy chain variable region and/or the immunoglobulin light chain variable region is defined further as comprising a nucleic acid sequence that encodes a cytotoxic protein and forms a fusion protein with the immunoglobulin heavy chain variable region and/or the immunoglobulin light chain variable region, or both under conditions so that the host cell expresses a polypeptide comprising the immunoglobulin heavy chain variable region and the immunoglobulin light chain variable region, thereby producing the antibody or the antigen-binding fragment of the antibody; and (b) purifying the antibody or the antigen-binding fragment of the antibody. In another aspect, the humanized antibody is expressed from nucleic acids SEQ ID NOS: 13 and 14, into amino acid sequences SEQ ID NOS:15 and 16.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
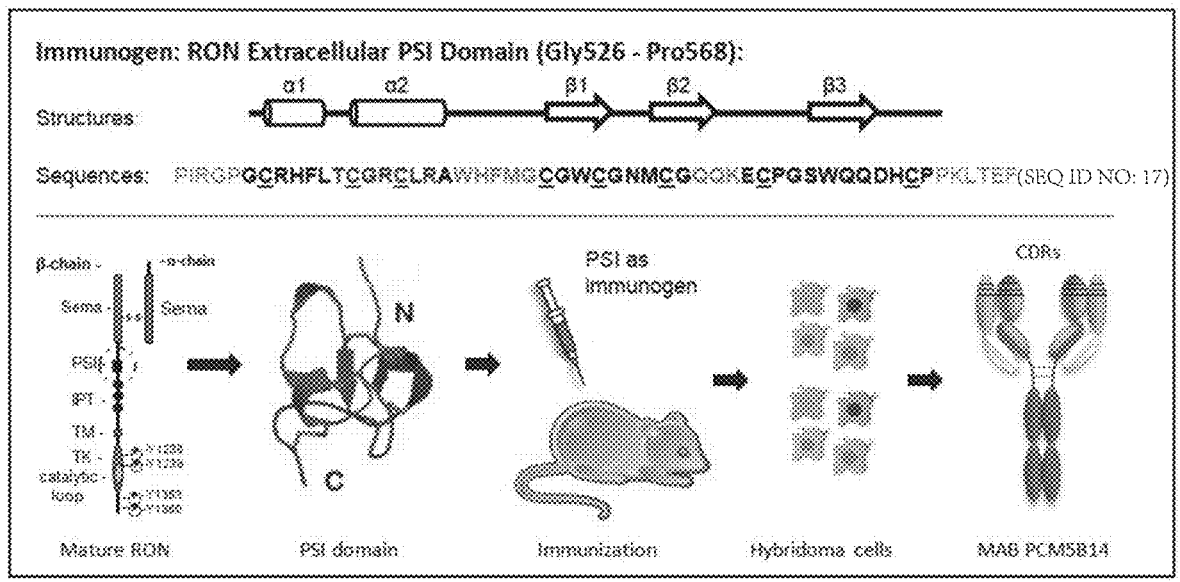
FIG. 1 shows the generation of monoclonal antibodies (MAB) specific to RON extracellular Plexin-Semaphorin-Integrin (PSI) Domain for inducing RON endocytosis of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventors have developed a number of anti-RON mAbs specific for the Plexin-Semaphorin-Integrin (PSI) domain that show biological and therapeutic effects in preclinical models. Anti-RON PSI domain mAbs in conjugation with chemoagents are effective in the delivery of cytotoxic drugs to targeted killing of cancer cells. In some instances, the PSI domain of RON can be referred to as $RON^{PSI}$.

The antibodies disclosed herein can be used to treat various forms of cancer, e.g., non-small cell lung cancer, breast, ovarian, prostate, cervical, colorectal, lung, pancreatic, gastric, and head and neck cancers. The cancer cells are exposed to a therapeutically effective amount of the antibody so as to inhibit or reduce proliferation of the cancer cell. In some embodiments, the antibodies inhibit cancer cell proliferation by at least 40%, 50%, 60%, 70%, 80%, 90%, 95%, 98%, 99%, or 100%.

The terms "a sequence essentially as set forth in SEQ TD NO:(#)", "a sequence similar to", "nucleotide sequence" and similar terms, with respect to nucleotides, refers to sequences that substantially correspond to any portion of the sequence identified herein as SEQ ID NO:1. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of anti-$RON^{PSI}$ antibodies. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

An oligonucleotide sequence that is "substantially homologous" to the anti-RON antibodies of SEQ NO:#" is defined herein as an oligonucleotide sequence that exhibits greater than or equal to 75%, 80%, 85%, 90%, 91%, 92%, 93%, 94%, 95%, 96%, 97%, 98%, 99%, or 100% identity to the sequence of SEQ ID NO:# when sequences having a length of 100 bp or larger are compared. Generally, conservative amino acid substitutions will be used to modify the sequences within the listed percentages. Conservative amino acid substitutions are well-known in the art.

The term "gene" is used to refer to a functional protein, polypeptide or peptide-encoding unit. As will be understood by those in the art, this functional term includes at least partially genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

The term "vector" refers to a nucleic acid molecule(s) that transfer DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome.

The terms "host cell", "recombinant cell", or "recombinant host" refer to cells that have been engineered to contain nucleic acid segments or altered segments, whether archeal, prokaryotic, or eukaryotic. Thus, engineered, or recombinant cells, are distinguishable from naturally occurring cells that do not contain recombinantly introduced genes.

The term "fusion protein" refers to a hybrid protein expressed by a nucleic acid molecule comprising nucleotide sequences of at least two genes. For example, a fusion protein can comprise at least part of a first and a second polypeptide fused with a polypeptide that binds an affinity matrix.

The term "antibody" encompasses polyclonal and monoclonal antibody preparations, as well as preparations including hybrid antibodies, altered antibodies, F(ab')2 fragments, F(ab) fragments, Fv fragments, single domain antibodies, chimeric antibodies, humanized antibodies, and functional fragments thereof which exhibit immunological binding properties of the parent antibody molecule.

The term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments that exhibit immunological binding properties of the parent monoclonal antibody molecule. In the case of the present invention, a number of hybridomas have been developed that, have unique binding properties with the PSI domain of RON (RON$^{PSI}$), e.g., they trigger specific internalization of RON into RON expressing cells, e.g., cancer cells. As used herein, the hybridoma PCM5B14 and the antibody produce PCM5B14.

Methods of making monoclonal antibodies are known in the art. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Monoclonal antibodies are generally prepared using the method of Kohler and Milstein, Nature (1975) 256:495-497, or a modification thereof. Typically, a mouse, hamster, or rat is immunized. The spleen and/or large lymph nodes are is removed and dissociated into single cells. B-cells and/or dissociated spleen cells are then induced to fuse with myeloma cells to form hybridomas (typically cells that do not express endogenous antibody heavy and/or light chains), and are cultured in, e.g., a selective medium (e.g., hypoxanthine, aminopterin, thymidine medium, "HAT"). The resulting hybridomas are plated by limiting dilution and assayed for the production of antibodies that bind specifically to RON. The selected monoclonal antibody-secreting hybridomas are then cultured either in vitro (e.g., in tissue culture bottles or hollow fiber reactors), or in vivo (e.g., as ascites in mice).

The term "antibody fragment" refers to a portion of an antibody such as F(ab') 2, F(ab) 2, Fab', Fab, and the like. Regardless of structure, an antibody fragment binds with the same antigen that is recognized by the intact antibody. For example, an anti-RON monoclonal antibody fragment binds with an epitope of RON.

The term "antibody fragment" refers to a synthetic or a genetically engineered polypeptide that binds to a specific antigen, such as polypeptides that include light chain variable region(s), "Fv" fragments that include the variable regions of the heavy and light chains, recombinant single chain polypeptide molecules in which light and heavy variable regions are connected by a peptide linker ("scFv proteins"), and minimal recognition units that include the amino acid residues that mimic the hypervariable region.

The term Fab' is defined herein as a polypeptide comprising a heterodimer of the variable domain and the first constant domain of an antibody heavy chain, plus the variable domain and constant domain of an antibody light chain, plus at least one additional amino acid residue at the carboxy terminus of the heavy chain $C_H1$ domain including one or more cysteine residues. $F(ab')_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, a short (about 1-10 residues) cysteine-containing polypeptide. In certain applications, a common naturally occurring antibody hinge sequence (cysteine followed by two prolines and then another cysteine) is used; this sequence is found in the hinge of human $IgG_1$ molecules (E. A. Kabat, et al., Sequences of Proteins of Immunological Interest 3rd edition (National Institutes of Health, Bethesda, Md., 1987)). In other embodiments, the hinge region is selected from another desired antibody class or isotype. In certain preferred embodiments of this invention, the C-terminus of the $C_H1$ of Fab' is fused to the sequence Cys X X X preferably is Ala, although it may be any other residue such as Arg, Asp, or Pro. One or both X amino acid residues may be deleted.

The "hinge region" is the amino acid sequence located between $C_H1$ and $C_H2$ in native immunoglobulins or any sequence variant thereof. Analogous regions of other immunoglobulins will be employed, although it will be understood that the size and sequence of the hinge region may vary widely. For example, the hinge region of a human IgG1 is only about 10 residues, whereas that of human IgG3 is about 60 residues.

The term Fv is defined to be a covalently or non-covalently associated heavy and light chain heterodimer which does not contain constant domains.

The term Fv-SH or Fab'-SH is defined herein as a Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogeneous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

The term "chimeric antibody" refers to a recombinant protein that contains the variable domains and complementary determining regions derived from a rodent antibody, while the remainder of the antibody molecule is derived from a human antibody.

The term "humanized antibody" refers to an immunoglobulin amino acid sequence variant or fragment thereof that is capable of binding to a predetermined antigen and that includes an FR region having substantially the amino acid sequence of a human immunoglobulin and a complementarity determining regions (CDR) having substantially the amino acid sequence of a non-human immunoglobulin or a sequence engineered to bind to a preselected antigen. Humanizing an antibody is often referred to as "veneering" an antibody with the CDRs in the variable regions of the heavy, light chain or both.

The term "antibody-drug conjugate" refers to antibodies or antibody fragments thereof, including antibody derivatives that bind to the PSI domain of RON and are conjugated to cytotoxic, cytostatic, and/or therapeutic agents. The term "therapeutic agent" refers to an agent that exerts a cytotoxic, cytostatic, and/or immunomodulatory effect on cancer cells or activated immune cells. Non-limiting examples of therapeutic agents include cytotoxic agents, chemotherapeutic agents, cytostatic agents, and immunomodulatory agents. The term "chemotherapeutic agent" refers to a chemical compound useful in the treatment of cancer. The term "cytotoxic effect" refers to the depletion, elimination, and/or the killing of a target cell(s) using the present invention. The term "cytotoxic agent" refers to an agent of the present invention that has a cytotoxic and/or cytostatic effect on a cell. The term "cytostatic effect" refers to the inhibition of cell proliferation using the present invention. The term "cytostatic agent" refers to an agent of the present invention that has a cytostatic effect on a cell, thereby inhibiting the growth and/or expansion of a specific subset of cells.

As discussed herein, minor variations in the amino acid sequences of antibodies or immunoglobulin polypeptides are contemplated, e.g., providing that the variations in the amino acid sequence maintain at least 75%, more preferably at least 80%, 90%, 95%, 96%, 97%, 98%, 99%, and 100% homology to the human framework regions of the heavy and/or light chain variable domain. Specifically, in the present invention if the humanized antibody maintains at least 95%, 96%, 97%, 98%, 99%, or 100% homology to the non-CDR portions of the human variable domain and the constant domain, then the humanized antibody is considered to be fully humanized.

Certain variations in the amino acid sequences are considered conservative amino acid substitutions. Conservative substitutions are those between amino acids with similar side chains. Amino acids are generally divided into families: (1) non-polar: alanine, valine, leucine, isoleucine, proline, phenylalanine, methionine, tryptophan; (2) acidic: aspartate, glutamate; (3) basic: lysine, arginine, histidine; and (4) polar: lysine, asparagine, glutamine, cysteine, serine, threonine, tyrosine. Additional amino acid families include: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. Thus, it is reasonable to expect that a single replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework region. Whether an amino acid change results in a functional peptide is readily determined by assaying the specific activity of the polypeptide derivative. Fragments or analogs of antibodies or immunoglobulin molecules can be readily prepared by those of ordinary skill in the art, including substitutions at the amino- and carboxy-terminus, including making fusion proteins with, e.g., cytotoxic proteins. Structural and functional domains can also be identified by comparison of the nucleotide and/or amino acid sequence data (as shown herein) and/or sequence databases. Computerized comparison methods can be used to identify sequence motifs or predicted protein conformation domains that occur in other proteins of known structure and/or function. Generally, conservative amino acid substitution will not substantially change the structural characteristics of the parent sequence (e.g., a replacement amino acid should not tend to break a helix that occurs in the parent sequence, or disrupt other types of secondary structure that characterizes the parent sequence).

The terms "cell" and "cell culture" are used interchangeably to refer to cell that are mostly but not always in a single cell suspension or attached to a plate or tissue, and include their progeny. The terms "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

The terms "protein", "polypeptide" or "peptide" refer to compounds comprising amino acids joined via peptide bonds and are used interchangeably.

The term "endogenous" refers to a substance the source of which is from within a cell. Endogenous substances are produced by the metabolic activity of a cell. Endogenous substances, however, may nevertheless be produced as a result of manipulation of cellular metabolism to, for example, make the cell express the gene encoding the substance.

The term "exogenous" refers to a substance the source of which is external to a cell. An exogenous substance may nevertheless be internalized by a cell by any one of a variety of metabolic or induced means known to those skilled in the art.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. The term "sequences" as used herein is used to refer to nucleotides or amino acids, whether natural or artificial, e.g., modified nucleic acids or amino acids. When describing "transcribed nucleic acids" those sequence regions located adjacent to the coding region on both the 5', and 3', ends such that the deoxyribonucleotide sequence corresponds to the length of the full-length mRNA for the protein as included. The term "gene" encompasses both cDNA and genomic forms of a gene. A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA I wherein cDNA 2 contains exon "B" instead). Because the two cDNAs contain regions of sequence identity they will both hybridize to a probe derived from the entire gene or portions of the gene containing sequences found on both cDNAs the two splice variants are therefore substantially homologous to such a probe and to each other.

The term "vector" is used in reference to nucleic acid molecules that transfer DNA segment(s) from one cell to another. The term "vehicle" is sometimes used interchangeably with "vector," The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The term a "pharmaceutically acceptable" refers to a component that is suitable for use with humans and/or animals without undue adverse side effects (such as toxicity, irritation, and allergic response) commensurate with a reasonable benefit/risk ratio.

The term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, to shrink or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

The term "pharmaceutical salts" refers to a salt for making an acid or base salts of a compounds. Examples of pharmaceutically acceptable salts include, but are not limited to, mineral or organic acid salts of basic residues such as amities; alkali or organic salts of acidic residues such as phenols. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The preferred phenolate salts are the alkaline earth metal salts, sodium, potassium or lithium.

The term "pharmaceutical carrier" refers to a pharmaceutically acceptable solvent, suspending agent or vehicle, for delivering the anti-RON antibodies, fragments thereof, and/ or Antibody drug conjugates (ADCs), compound to the animal or human. The carrier may be liquid or solid and is selected with the planned manner of administration in mind. Liposomes are also a pharmaceutical carrier.

The term "cancer" refers to all types of cancer or neoplasm or malignant tumors found in mammals, including carcinomas and sarcomas that express RON. Examples of cancers are cancer of the brain, breast, cervix, pancreatic, skin, prostate, liver, bladder, colon, head neck, kidney, lung, non-small cell lung, melanoma, mesothelioma, ovary, sarcoma, stomach, uterus and medulloblastoma.

Generation of monoclonal antibodies targeting the RON extracellular PSI domain: The RON extracellular PSI domain acts as a hinge during RON activation, which facilitates Cell surface RON internalization. A peptide containing 61 amino acids covering the entire the RON PSI domain was used as the immunogen for mice immunization. Hybridoma cells were screened for monoclonal antibodies that recognize the PSI domain and are able to induce robust RON internalization by cancer cells. A clone designated as PCM5B14 was selected as the lead candidate. FIG. 1 shows the generation of Monoclonal Antibodies (MAB) specific to RON extracellular Plexin-Semaphorin-Integrin (PSI) Domain for inducing RON endocytosis of the present invention.

Figure 2:
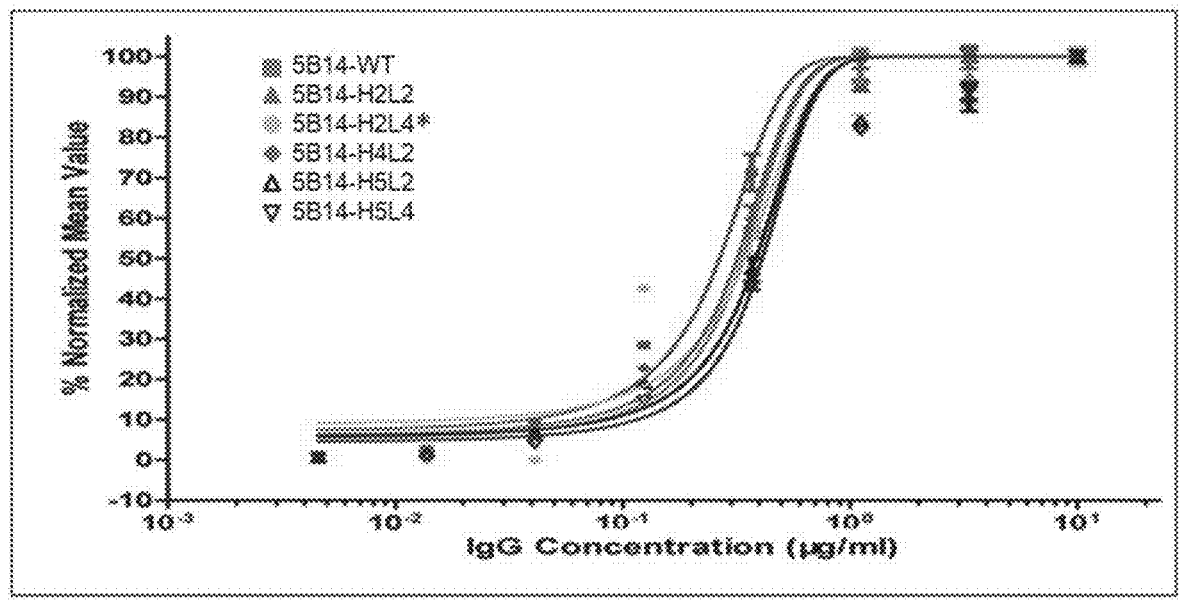
FIG. 2 is a graph that shows the specific binding affinity of humanized anti-RON MAB PCM5B14 (H5B14) to RON receptor.
Figure 4:
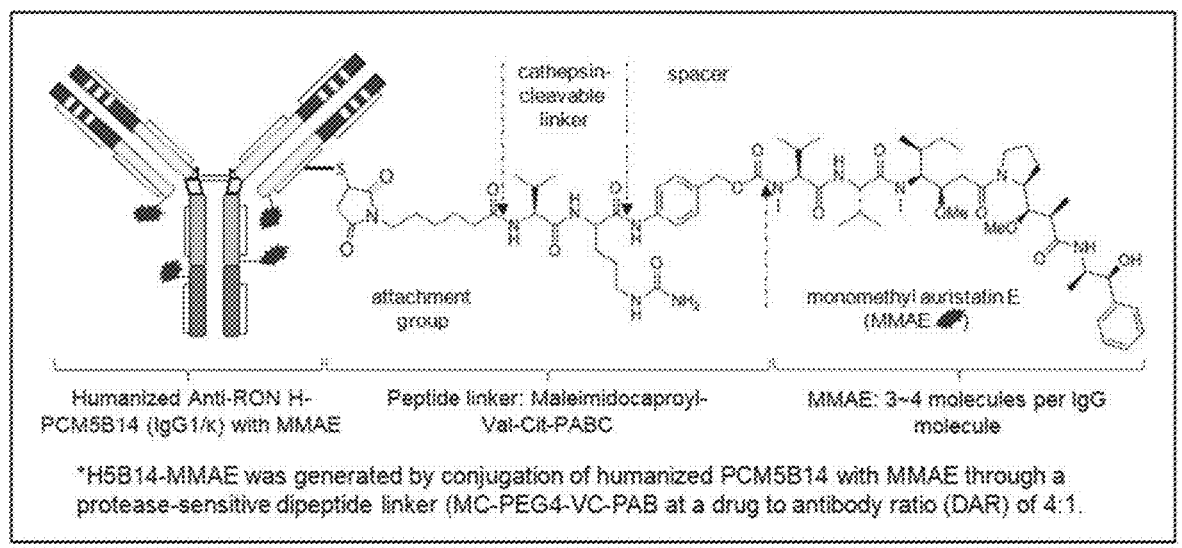
FIG. 4 shows the structure of H5B14 in conjugation with an exemplary cytotoxic chemotherapeutic to form antibody-drug conjugate for drug delivery (Monomethyl Auristatin E, MMAE as an example)
Figure 5:
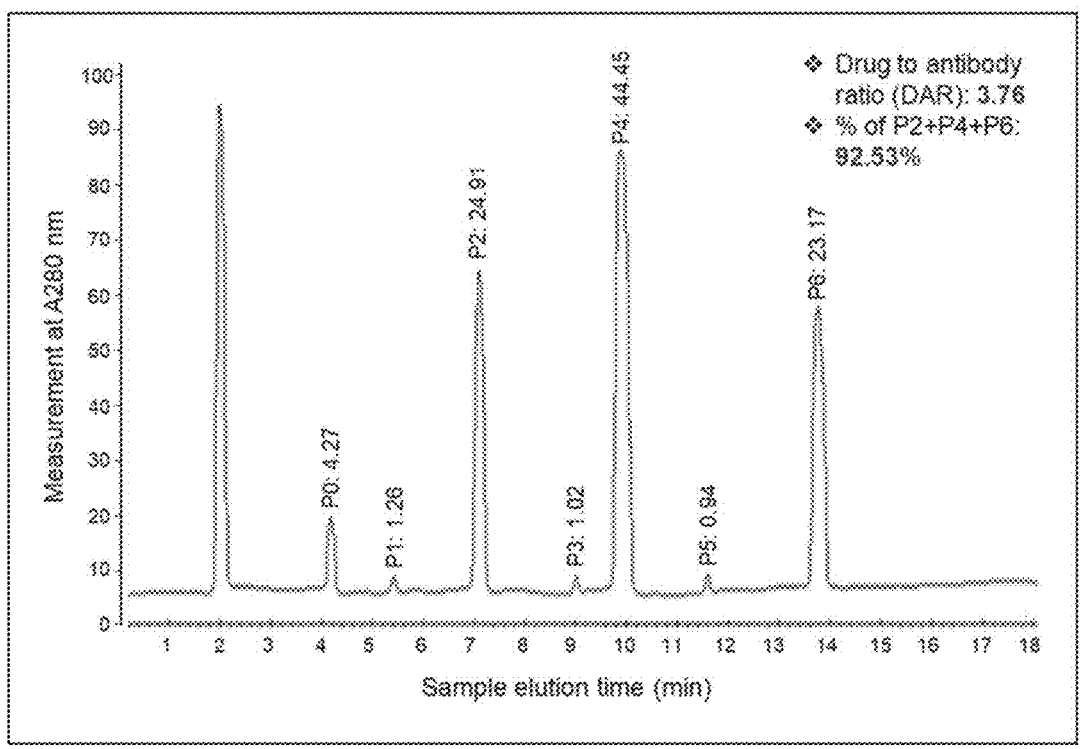
FIG. 5 is a graph that shows analysis of conjugation ratio of H5B14 with cytotoxic chemotherapeutics using hydrophobic interaction chromatography.
Figure 6:
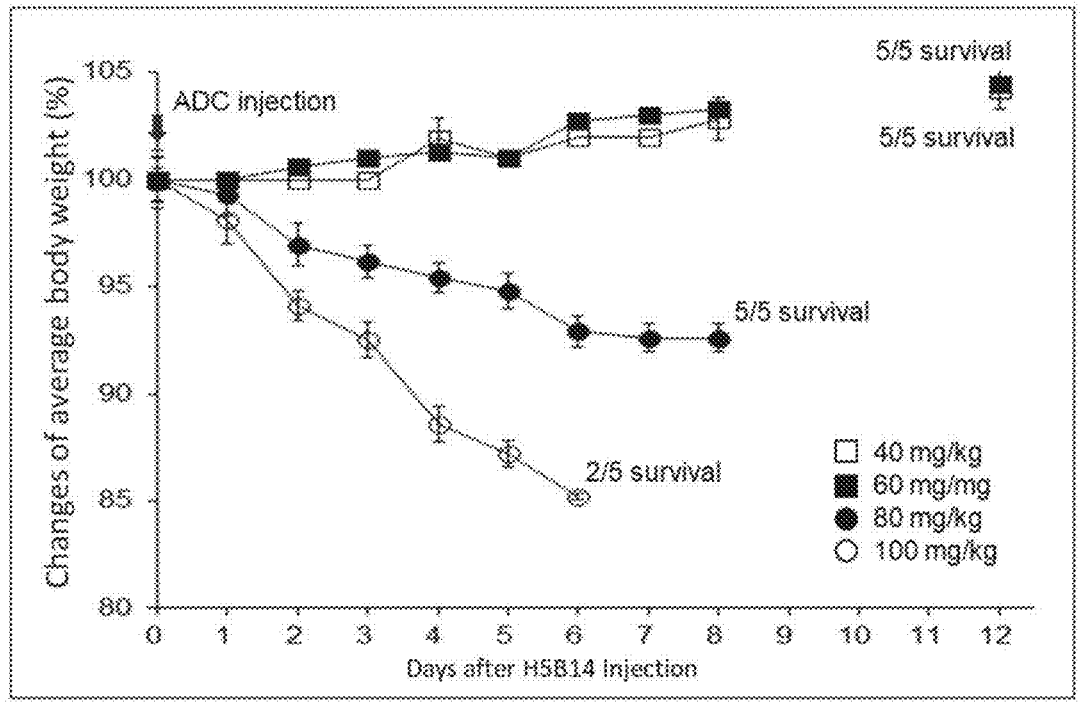
FIG. 6 is a graph that shows toxicological effect of H5B14-drug conjugates on mouse body weight and survival.

Humanization of PCM5B14 and generation of antibody-drug conjugate (ADC): Humanization was performed by grafting the complementarity-determining regions (CDRs) from both heavy and light chains of PCM5B14 into human IgG1/κ, acceptor frameworks to generate five light and five heavy chains to create 25 different parings of humanized IgG1/κ (molecules. Individual humanized PCM5B14s were analyzed for specificity, sensitivity, and binding affinities (FIG. 2). Humanized PCM5B14 H2L4 was selected (IgG1/ κ, designated as H5B14) for drug conjugation. Chemotherapeutics including doxorubicin, maytansinoid derivatives, monomethyl auristatin E (MMAE), and duocarmycin were used. H5B14 conjugated with MMAE (H5B14-MMAE) was selected as the ADC model for further study (FIG. 4). In FIG. 4, the H5B14-MMAE was generated by conjugation of humanized PCM5B14 with MMAE through a protease-sensitive di-peptide linker (MC-PEG4-VC-PAB) at a drug concentration to antibody ratio (DAR) of 4:1.

Figure 3:
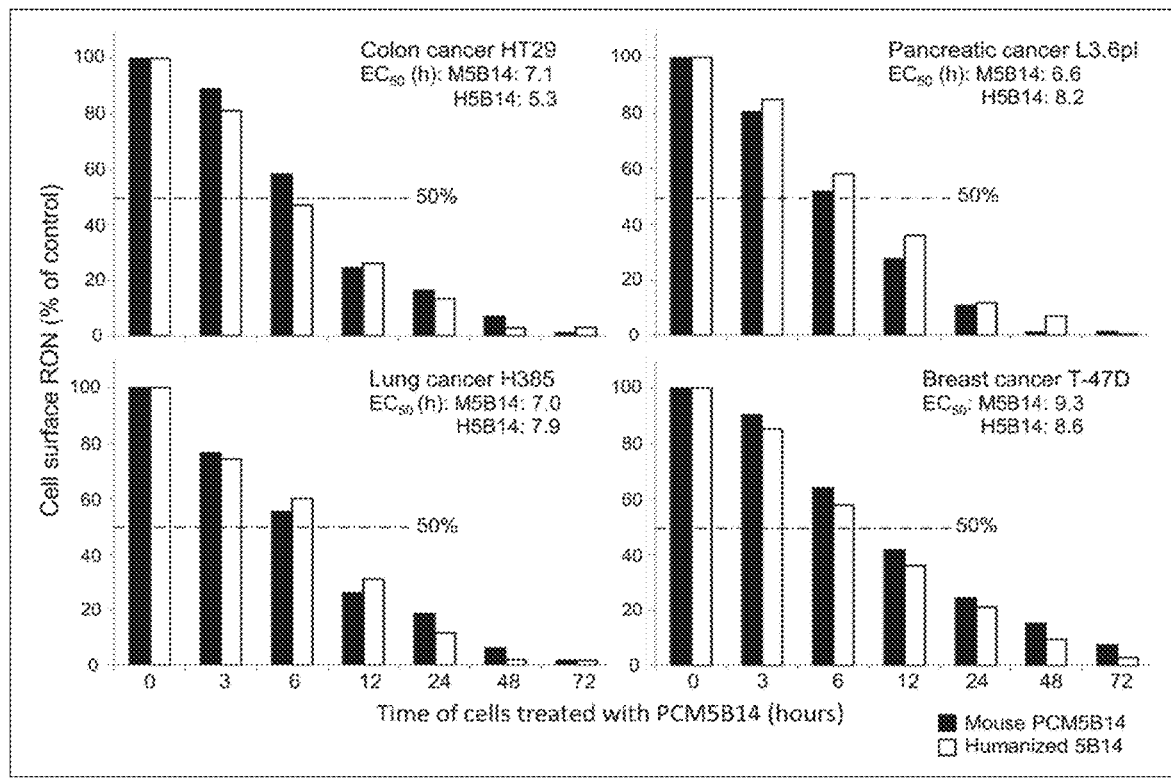
FIG. 3 shows the robust effect of H5B14 in induction of cell surface RON internalization by cancer cells.
Figure 7:
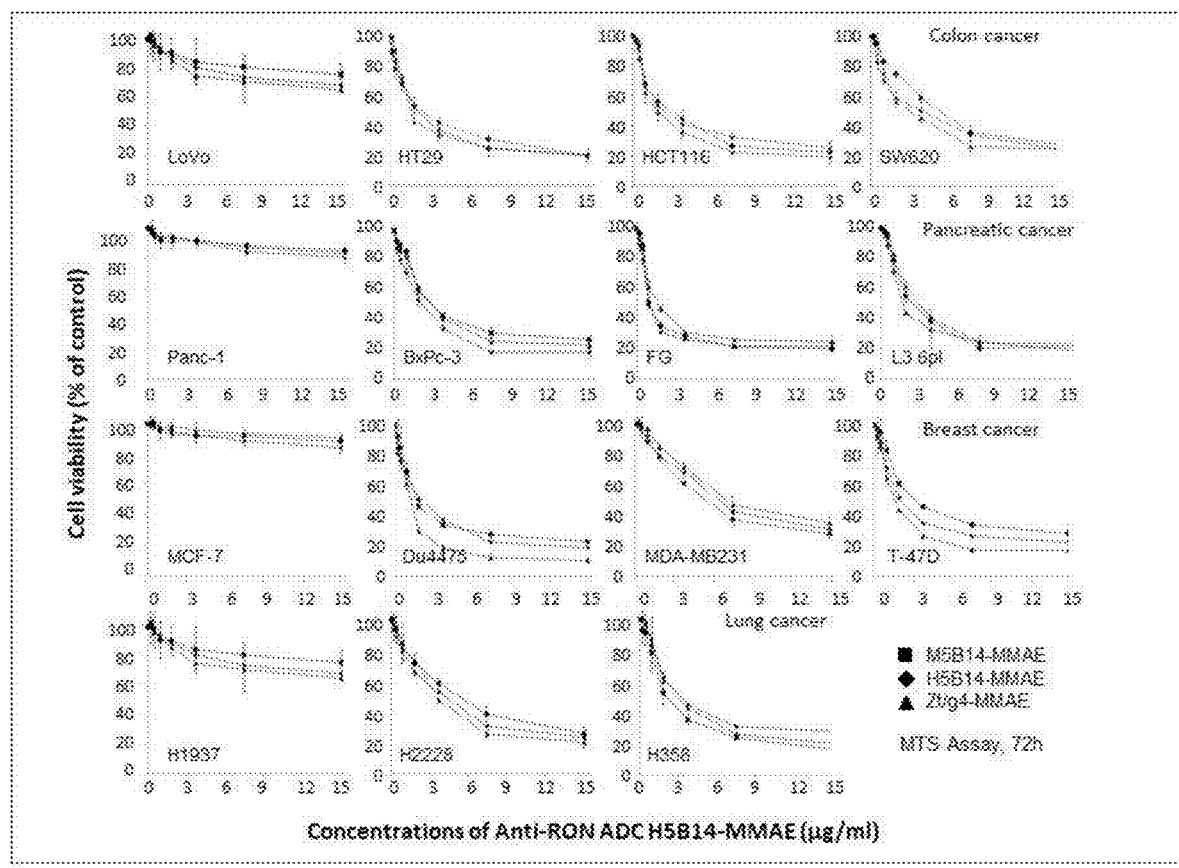
FIG. 7 are graphs that show the cytotoxic effect of H5B14-MMAE in vitro on different types of human cancer cell lines.
Figure 8:
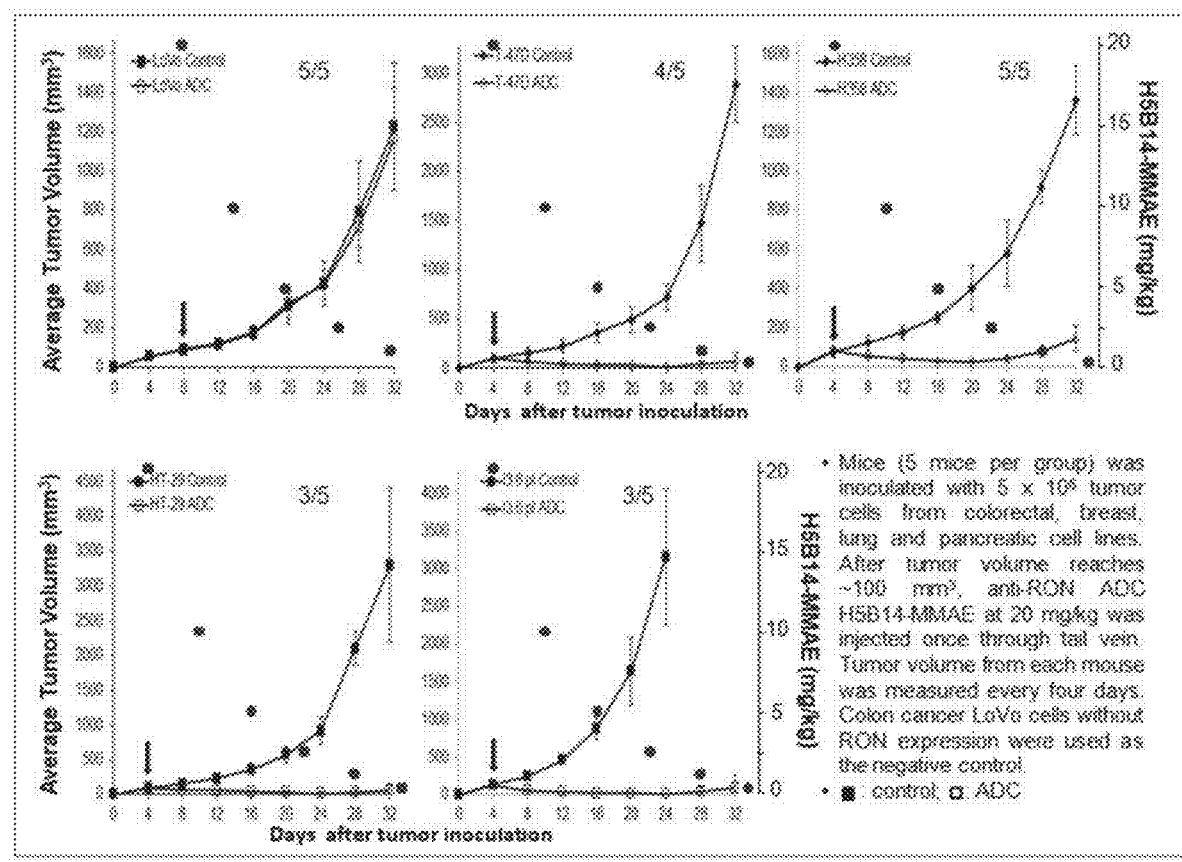
FIG. 8 are graphs that show the therapeutic efficacy of H5B14-MMAE in vivo in human xenograft tumors in mouse models.
Figure 9:
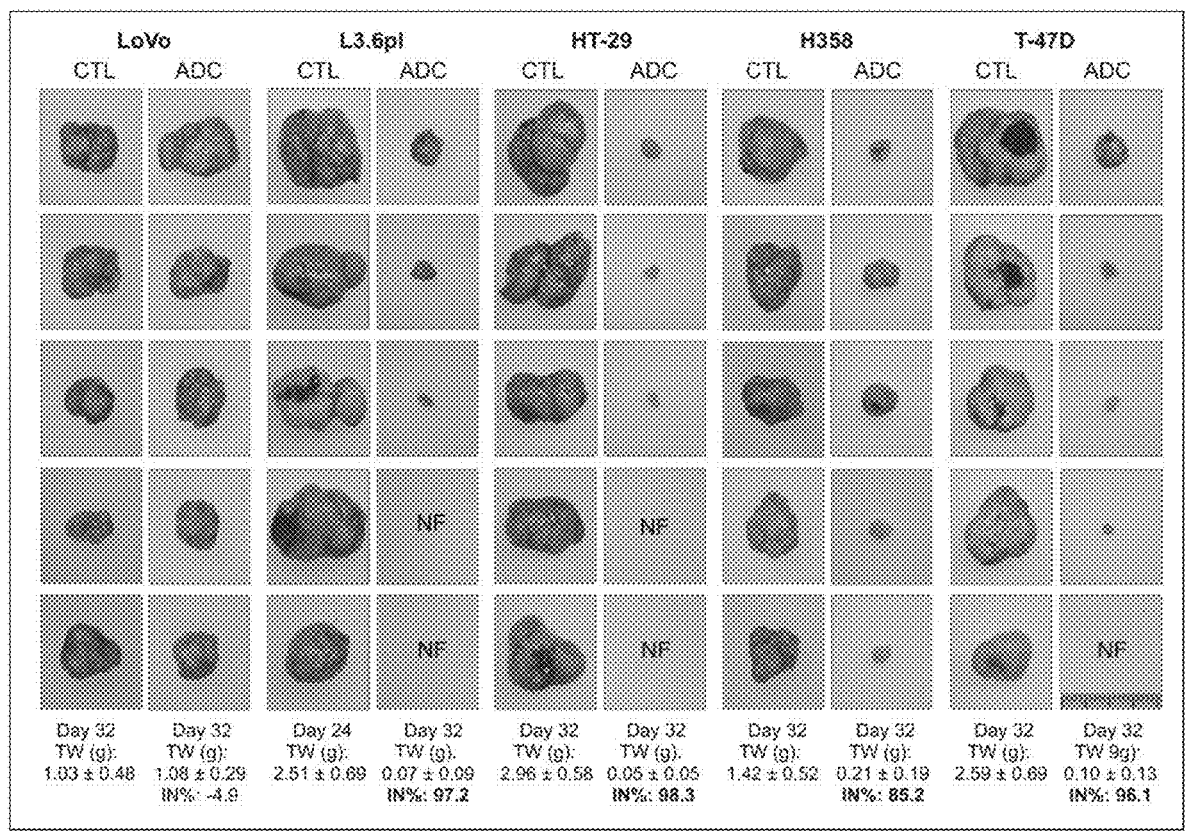
FIG. 9 shows the therapeutic effect of H5B14-MMAE in vivo on the weight of human xenograft tumors in mouse models.

Validation of H5B14 in induction of cell surface RON internalization by cancer cells: A panel of 15 human cancer cell lines from breast, colon, lung, and pancreatic tumors representing different levels of RON expression were used as the model to determine the effectiveness of H5B14 in induction of cell surface RON internalization. Representative results confirming the H5B14-induced robust RON internalization are shown in FIG. 3, The obtained results demonstrate that H5B14 is highly effective in causing RON endocytosis, which lead to delivery of sufficient amounts of cytotoxic drugs for cancer cell killing. Moreover, H5B14 targeting the RON PSI domain for receptor endocytosis in terms of the internalization efficacy ($IE_{50}$: the minimal time required to induce a 50% of RON internalization) is far more superior to other anti-RON antibodies. Therapeutic efficacy of H5B14-directed delivery of MMAE in killing cancer cells in vitro and eradicating xenograft tumors in vivo: The effect of H5B14-MMAE in killing cancer cells were confirmed in vitro using human cancer cell lines derived from breast, colon, lung, and pancreatic cancers (FIG. 7). The therapeutic efficacy of H5B14-MMAE in vivo was validated using tumor xenografts derived from human breast, colon, lung, and pancreatic cancer cell lines in mouse models (FIGS. 8 and 9).

Detailed Summary of Action of a Novel Anti-RON Monoclonal Antibody (H5B14) Recognizing the $RON^{PSI}$ domain for Cytotoxic Drug Delivery in Targeted Cancer Therapy.

Generation of monoclonal antibodies targeting the RON extracellular PSI domain for induction of robust RON internalization: Mice were immunized with RON proteins containing specific PSI domains in the RON extracellular sequences. Hybridoma cells were screened for monoclonal antibodies that are specific to the RON PSI domain and able to induce robust RON internalization by cancer cells. A clone designated as PCM5B14 was selected as the lead candidate.

Humanization of PCM5B14 and generation of antibody-drug conjugate (ADC): Humanization was performed by grafting the complementarity-determining regions (CDRs) from both heavy and light chains of PCM5B14 into human IgG1/κ acceptor framework to generate five light chains and five heavy chains to create 25 different parings of H5B14 IgG1/κ molecules. Individual humanized PCM5B14s were analyzed for specificity, sensitivity, and binding affinities. Humanized PCM5B14 H2L4 was selected (IgG1/κ, designated as H5B14) for drug conjugation. Chemotherapeutics including doxorubicin, maytansinoid derivatives, monomethyl auristatin E (MMAE), and duocarmycin were used. H5B14 was conjugated with MMAE (H5B14-MMAE) as the model for further study.

Therapeutic efficacy of H5B14-MMAE in killing cancer cells in vitro and eradicating xenograft tumors in vivo. The effect of H5B14-MMAE in killing cancer cells were confirmed in vitro using human cancer cell lines derived from breast, colon, lung, and pancreatic cancers. The therapeutic efficacy of H5B14-MMAE in vivo was validated using tumor xenografts derived from human breast, colon, lung, and pancreatic cancer cell lines in mouse models.

The PSI motif in the RON extracellular domain acts as a hinge that facilitates cell surface RON dimerization followed by internalization in cancer cells. To generate monoclonal antibodies specific to the RON PSI domain, a sequence containing 54 amino acids covering the entire PSI domain was synthesized as antigen for mouse immunization. Analyses of various hybridoma cells lead to identification of a mAb designated as clone PCM5B14, which specifically recognizes the $RON^{PSI}$ domain without cross-reactivity to other homologue proteins. PCM5B14 was then selected for further development.

Results from these studies demonstrate that generation of MABs specific to the RON extracellular PSI motif provides the pharmaceutical basis for using PCM5B14 to induce robust RON internalization for drug d for targeted drug delivery.

DNA Sequences:
CDRs from PCM5B14 VH (Heavy Chain variable region):

```
CDR1:
                                    (SEQ ID NO: 1)
GGCTACACCTTCACAGACTATCACATGGAT (30 nt)

CDR2:
                                    (SEQ ID NO: 2)
GACATCAACCCAAACAATGGCGGCGCCATCTACAATCAGAAGTTTAAGGG
C (51 nt)

CDR3:
                                    (SEQ ID NO: 3)
TGTCACTACGATTATGCTGGAGGAGCTTGGTTCGCTTAC (39 nt)
```

CDRs from PCM5B14 VL (Light Chain variable region):

```
CDR1:
                                    (SEQ ID NO: 4)
AAGAGCTCCCAGAGCCTGCTGTTCTCCGGCAACCAGAAGAATTACCTGGC
T (51 nt)

CDR2:
                                    (SEQ ID NO: 5)
TGGGCTTCTACCAGAGCTAGC (21 nt)

CDR3:
                                    (SEQ ID NO: 6)
CAGCAGTACTATAGCTTCCCAAGAACC (27 nt)
```

Amino Acid Sequences:

```
CDRs from PCM5B14 VH (Heavy Chain variable
region):
CDR1:
                                    (SEQ ID NO: 7)
GYTFTDYHMD (10aa)

CDR2:
                                    (SEQ ID NO:8)
DINPNNGGAIYNQKFKG (17aa)

CDR3:
                                    (SEQ ID NO: 9)
SHYDYAGGAWFAY (13aa)

CDRs from PCM5B14 VL (Light Chain variable
region):
CDR1:
                                    (SEQ ID NO: 10)
KSSQSLLFSGNQKNYLA (17aa)

CDR2:
                                    (SEQ ID NO: 11)
WASTRAS (7aa)
```

CDR3: QQYYSFPRT (9aa) (SEQ ID NO:12)

FIG. 2 shows the Specific Binding Affinity of Humanized Anti-RON MAB PCM5B14 (H5B14) to RON Receptor. Colon cancer HT29 cell line expressing ~19,000 RON molecules per cell were used as the model. Mouse PCM5B14 was used as the positive control. Individual H5B14 clones at different concentrations were incubated with cells followed by addition of FITC-coupled anti-human IgG1 antibody. Fluorescence intensities from individual samples were analyzed using the BD flow cytometer. Results in FIG. 2 are the dose-dependent specific binding of individual H5B14s. According to the obtained results, we selected H5B14H2L4 with the binding affinity at EC50 of 0.3456 μg/ml was the lead candidate. Results in Table 1 show the individual values reflecting the binding affinity and sensitivity of individual H5B14 clones to human RON receptor.

Table 1 shows the individual values reflecting the binding affinity and sensitivity of individual H5B14 clones to human RON receptor.

H5B14 is versatile for conjugation with various cytotoxic chemotherapeutics through various chemical conjugation methods. An example shown in FIG. 4, is the conjugation of H5B14 randomly with MMAE at the defined drug to antibody ratio (DAR, 4:1) through a protease-sensitive dipeptide linker (Maleimidocaproyl-Val-Cit-PABC, commercially available). MMAE is a highly potent tubulin inhibitor that blocks cellular mitosis leading to cell death.

| Bing Property | 5B14-WT | 5B14-H2L2 | 5B14-H2L4* | 5B14-H4L2 | 5B14-H5L2 | 5B14-H5L4 |
|---|---|---|---|---|---|---|
| Best-fit values | | | | | | |
| LogEC50(μg/ml) | 0.2653 | 0.3361 | 0.3456 | 0.3182 | 0.386 | 0.4108 |
| HillScope | 4.193 | 3.695 | 2.921 | 3.728 | 3.167 | 3.231 |
| EC50 | 1.842 | 2.168 | 2.216 | 2.081 | 2.432 | 2.575 |
| Std. Error | | | | | | |
| LogEC50 | 0.01448 | 0.01198 | 0.05194 | 0.01157 | 0.03217 | 0.03578 |
| HillScope | 0.3864 | 0.3051 | 0.816 | 0.285 | 0.6132 | 0.7205 |

Results from these studies demonstrate that humanized PCM5B14, including the clone H2L4 is highly specific and sensitive to human RON. FIG. 3 shows the Robust Effect of H5B14 in Induction of Cell Surface RON Internalization by Cancer Cells.

Human cancer cell lines including H129, L3.6pl, H358, and T-47D cells expressing RON receptors in the range of 10,000 to 19,000 molecules per cells, respectively, were used as the model. Cells were incubated with 5 μg/ml of H5B14 for various times. Mouse anti-RON antibodies Zt/g4, PCM5B14, and humanized Zt/g4 were used as the control. After removing the bound antibodies in the cell surface by acidic buffer, the remaining cell surface RON was detected by anti-RON mAb Zt/f2 followed by FITC-coupled goat anti-mouse IgG1 antibody. Immunofluorescence intensities from individual samples were analyzed using the BD flow cytometer. The minimal time (hours) required to reach a 50% reduction of cell surface RON was defined as the $EC_{50}$.

Results from these studies demonstrated that H5B14 specific to the RON PSI domain is superior in induction of cell surface RON internalization with EC50 from 5.3 to 8.2 hours depending on individual 15 cancer cell lines. Table 2 shows that clone H5B14 had superior binding characteristics for inducing cell surface endocytosis by cancer cells when compared to other antibodies.

Table 2 shows that clone H5B14 had superior binding characteristics for inducing cell surface endocytosis by cancer cells when compared to other antibodies.

| | Internalization efficacy of cell surface RON ($EC_{50}$, hours) | | | |
|---|---|---|---|---|
| Anti-RON-ADCs | Colon HT-29 | Breast T-47D | Pancreatic L3.6p1 | Lung H358 |
| Mouse Zt/g4 | 11.02 ± 0.75 | 23.46 ± 1.24 | 14.14 ± 0.77 | 7.47 ± 0.48 |
| Humanized Zt/g4 | 12.35 ± 1.13 | 21.70 ± 0.89 | 11.61 ± 0.69 | 9.44 ± 0.71 |
| Mouse PCM5B14 | 7.11 ± 0.45 | 9.28 ± 0.78 | 6.59 ± 0.34 | 7.02 ± 0.82 |
| Humanized 5B14 | 5.33 ± 0.23 | 8.26 ± 0.62 | 8.17 ± 0.44 | 7.94 ± 0.36 |

FIG. 4 shows the structures of H5B14 in Conjugation with Cytotoxic Chemotherapeutics to Form Antibody-Drug Conjugate for Targeted Drug Delivery (Monomethyl Auristatin E, MMAE as an example).

FIG. 5 shows an analysis of Conjugation Ratio of H5B14 with Cytotoxic Chemotherapeutics Using Hydrophobic Interaction Chromatography. In FIG. 5, H5B14-MMAE conjugates were first purified using a PC10 Sephadex G25 column and then sterilized through a 0.22 μM filter. The conjugation ratio was verified by hydrophobic interaction chromatography using a Varian Prostar 210 Quaternary HPLC system coupled with a TSK butyl-NPR. 4.6×3.5 column (Tosoh Biosciences, Prussia, Pa.). The number of MIME conjugated to Zt/g4 was determined based on molecular size and elution time, Individual H5B14-MMAEs with different numbers of MMAE (0 to 8) are marked as P0 to P8. Results from this analysis demonstrate that by controlling the chemical reactions to reach a defined DAR, H5B14 in conjugation with cytotoxic drug is highly efficient with average of DAR at 3.76, which is required to show the maximal cytotoxicity against cancer cells. Results from these studies demonstrate that H5B14 is suitable for conjugation with various cytotoxic chemotherapeutics at the defined drug to antibody ratio.

FIG. 6 is a graph that shows the toxicological effect of H5B14-Drug Conjugates on Mouse Body Weight and Survival.

To determine the toxic effect and the maximal tolerated dose (MTD) of H5B14-MMAE, mouse was selected as the model. To this end, Balb/C mice (5 animals per group) were injected once with H5B14-MMAE at different doses through the tail vein. Individual mouse body weights were measured accordingly to reach the average body weight for each group. Mouse body weight (~18-20 g per mouse) before injection was set as 100%. Daily activities, body weight, and animal death were monitored daily.

Results from these studies demonstrate that H5B14-MMAE at therapeutic doses has not toxic activity. Also, H5B14-MMAE is well tolerated in mice with MTD at ~60 mg/kg. An increase in H5B14-MMAE up to 80 mg/kg has visible toxicities with significant reduction in the average mouse body weight.

FIG. 7 are graphs that show the cytotoxic effect of H5B14-MMAE in vitro on different types of human cancer cell lines. A panel of twelve human cancer cell lines including those from colon, breast, lung and pancreatic cancers were tested in vitro for H5B14-MMAE-induced cell death. Three cancer cell lines without RON expression were used as the control. Also, mouse PCM5B14-MMAE and Zt/g4-MMAE (another anti-RON ADC) were used for comparisons. Cells were treated with different amounts of H5B14-MMAE in triplicate for 72 hours. Cells viabilities were determined by the standard MTS assay. Results from these studies demonstrated that H5B14-MMAE is highly specific to cancer cells expressing ROT. The minimal amounts of H5B14-MMAE required to killing 50% of cancer cells ($IC_{50}$) are in the ranges of 1 μg/ml to 3 μg/ml dependent on individual cell lines.

FIG. 8 shows the Therapeutic Efficacy of H5B14-MMAE in vivo in Human Xenograft Tumors in Mouse Models. Xenograft tumors mediated by four human cancer cell lines representing colon, lung, breast, and pancreatic cancers were established in athymic nude mice (ten mice per group). In each group, the control mice were treated with normal human IgG and the experimental mice were treated with a single dose of H5B14-MMAE at 20 mg/kg. Results from these studies demonstrate that H5B14-MMAE is highly effective in inhibition and/or eradicate xenograft tumors derived from different types of cancer cells. The calculated tumoristatic concentrations (the minimal doses of H5B14-MMAE required to reach a balance between tumor growth and tumor inhibition, TSC) are in the range of 1 to 3 mg/kg body weight. Moreover, no toxic activities were observed in all mice treated with the dose of H5B14-MMAE.

FIG. 9 shows the Therapeutic Effect of H5B14-MMAE in vivo on the Weight of Human Xenograft Tumors in Mouse Models. Xenograft tumors mediated by four human cancer cell lines representing colon, lung, breast, and pancreatic cancers were established in athymic nude mice (ten mice per group). In each group, the control mice were treated with normal human IgG and the experimental mice were treated with a single dose of H5B14-MMAE at 20 mg/kg. At the end of experiments day 24 or day 32, mice were sacrificed. Individual tumors from each group were collected and weighted to obtain the average tumor weight for each group. The percentages of tumor growth inhibition were calculated accordingly. Results from these studies demonstrate that H5B14-MMAE not only inhibits xenograft tumor growth but also eradicate tumors. The calculated tumor growth inhibition based on the average tumor weight between control and experimental groups are in the range of 85% to 98% dependent on individual tumor models.

Complete Humanized Anti-RON PCM5B14 IgG1/κ Sequences (Subtype H2L4).

Complete Nucleotide Sequences of Humanized PCM5B14 Heavy Chain (IgG1): 1425 nt (SEQ ID NO:13), the Kozak sequence is underlined, the leader peptide is underlined and italicized, the CDRs are in bold, and the CH1-CH2-CH3 domains are italicized.

Kozak sequence—Leader peptide—VH (CDR1-CDR2-CDR3)—CH (CH1-CH2-CH3)—Stop

<u>GCCGCCACC</u><u>*ATGGGTTGGTCATGTATTATTCTGTTTCTGGTGGCTACTGC*</u>

<u>*TACCGGCGTGCATTCC*</u>CAGGTGCACGCTGGTCCAGTCTGGGGCTGAAGTG

AAGAAGCCCGGCGCCACCGTGAAGATCAGCTGCAAGGTGTCCGGCTACAC

CTTCACAGACTATCACATGGATTGGGTGCAGCAGGCTCCTGGCAAGGGCC

TCGAGTGGATGGGCGACATCAACCCAAACAATGGCGGCGCCATCTACAAT

CAGAAGTTTAAGGGCCGGGTGACCATCACAGCTGACACCTCTACAGATAC

CGCCTATATGGAGCTGAGCTCCCTGAGATCCGAGGACACAGCCGTGTACT

ATTGCGCCCGGTCTCACTACGATTATGCTGGAGGAGCTTGGTTCGCTTAC

*TGGGGACAGGGCACACTGGTGACCGTGAGCCGGGCTTCCACCAAGGGCCC*

*TAGCGTGTTTCCACTGGCCCCCTCTTCCAAGTCTACAAGCGGAGGAACCG*

*CCGCTCTGGGATGTCTGGTGAAGGATTACTTCCCAGAGCCCGTGACCGTG*

*TCTTGGAACAGCGGCGCTCTGACAAGCGGCGTGCACACATTTCCTGCCGT*

*GCTGCAGTCCTCTGGCCTGTACTCCCTGAGCTCCGTGGTGACAGTGCCAT*

*CTAGCTCCCTGGGCACACAGACCTATATCTGCAACGTGAATCACAAGCCA*

*AGCAATACCAAGGTGGACAAGAAGGTGGAGCCCAAGTCCTGTGATAAGAC*

*ACACACCTGCCCCCCTTGTCCTGCTCCAGAGCTGCTGGGAGGACCTTCCG*

*TGTTCCTGTTTCCACCCAAACCTAAGGACACACTGATGATCTCTCGGACA*

*CCAGAGGTGACCTGCGTGGTGGTGGACGTGAGCCACGAGGATCCCGAGGT*

*GAAGTTCAACTGGTATGTCGATGGCGTGGAGGTGCACAATGCCAAGACCA*

*AGCCCCGGGAGGAGCAGTACAACTCTACATATAGGGTGGTGAGCGTGCTG*

*ACCGTGCTGCACCAGGACTGGCTCAACGGCAAGGAGTATAAGTGCAAGGT*

*GTCCAATAAGGCTCTGCCCGCCCCTATCGAGAAGACAATCTCTAAGGCTA*

*AGGGCCAGCCTAGGGAGCCACAGGTGTACACCCTGCCTCCATCTAGAGAC*

*GAGCTGACAAAGAACCAGGTGAGCCTGACCTGTCTGGTGAAGGGCTTCTA*

*TCCCAGCGATATCGCCGTGGAGTGGGAGTCCAATGGCCAGCCTGAGAACA*

*ATTACAAGACCACACCCCCTGTGCTGGACTCCGATGGCTCTTTCTTTCTG*

*TATTCCAAGCTGACCGTGGATAAGTCTCGGTGGCAGCAGGGCAACGTGTT*

*CAGCTGTTCTGTGATGCACGAAGCCCTGCATAATCACTATACCCAGAAAT*

*CCCTGAGTCTGTCACCTGGAAATGA*

Complete Nucleotide Sequences of Humanized PCM5BL4 Light Chain (κ): 729 nt (SEQ ID NO:14)

the Kozak sequence is underlined, the leader peptide is underlined and italicized, the CDRs are in bold, and the CL domain is italicized.

Kozak sequence—Leader peptide—VL (CDR1-CDR2-CDR3)—CL—Stop

<u>GCCGCCACC</u><u>*ATGGGCTGGTCATGTATTATTCTGTTTCTGGTCGCAACTGC*</u>

<u>*TACTGGGGTGCATAGC*</u>GAAATCGTGATGACTCAGTCTCCCGGAACCCTGT

CCCTGTCTCCAGGCGAGCGGGCCACCCTGTCCTGCAAGAGCTCCCAGAGC

CTGCTGTTCTCCGGCAACCAGAAGAATTACCTGGCTTGGTATCAGCAGAA

GCCAGGCCAGGCTCCCAGGCTGCTGATCTACTGGGCTTCTACCAGAGCTA

GCGGCATCCCCGACAGGTTCAGCGGCTCCGGCTCTGGCACAGACTTCACC

CTGACAATCTCTAGACTGGAGCCTGAGGACTTCGCCGTGTACTATTGCCA

GCAGTACTATAGCTTCCCAAGAACCTTTGGCCAGGGCACAAAGCTGGAGA

TCAAGCGGACCGTGGCCGCTCCCAGCGTGTTCATCTTTCCCCCTTCCGAC

GAGCAGCTGAAGTCCGGCACAGCTTCTGTGGTGTGCCTGCTGAACAACTT

CTACCCCAGGGAGGCCAAGGTCCAGTGGAAGGTGGATAACGCTCTGCAGA

GCGGCAATTCCCAGGAGTCTGTGACCGAGCAGGACAGCAAGGATTCCACA

TATTCTCTGTCTAGCACCCTGACACTGTCTAAGGCCGATTACGAGAAGCA

CAAGGTGTATGCTTGTGAAGTCACCCACCAGGGTCTGTCATCACCCGTCA

CTAAGTCTTTTAACCGAGGCGAATGCTGA

Complete Amino Acid Sequences of Humanized PCM5B14
Heavy Chain (IgG1): 471 amino acids
(SEQ ID NO:15), methionines underlined, *-stop.

```
MGWSCIILFL VATATGVHSO VQLVQSGAEV KKPGATVKIS

CKVSGYTFTD YHMDWVQQAP GKGLEWMGDI NPNNGGAIYN

QKFKGRVTIT ADTSTDTAYM ELSSLRSEDT AVYYCARSHY

DYAGGAWFAY WGQGTLVTVS RASTKGPSVF PLAPSSKSTS

GGTAALGCLV KDYFPEPVTV SWNSGALTSG VHTFPAVLQS

SGLYSLSSVV TVPSSSLGTQ TYICNVNHKP SNTKVDKKVE

PKSCDKTHTC PPCPAPELLG GPSVFLEPPK PKDTLMISRT

PEVTCVVVDV SHEDPEVKFN WYVDGVEVHN AKTKPREEQY

NSTYRVVSVL TVLHQDWLNG KEYKCKVSNK ALPAPIEKTI

SKAKGQPREP QVYTLPPSRD ELTKNQVSLT CLVKGFYPSD

IAVEWESNGQ PENNYKTTPP VLDSDGSFFL YSKLTVDKSR

WQQGNVESCS VMHEALHNHY TQKSLSLSPG K*
```

Complete Amino Acid Sequences of Humanized PCM5B14
Light Chain (κ): 239 amino acids
(SEQ ID NO:16), methionines underlined, *-stop.

```
MGWSCIILFL VATATGVHSE IVMTQSPGTL SLSPGERATL

SCKSSQSLLF SGNQKNYLAW YQQKPGQAPR LLIYWASTRA

SGIPDRFSGS GSGTDFTLTI SRLEPEDFAV YYCQQYYSFP

RTFGQGTKLE IKRTVAAPSV FIFPPSDEQL KSGTASVVCL

LNNFYPREAK VQWKVDNALQ SGNSQESVTE QDSKDSTYSL

SSTLTLSKAD YEKHKVYACE VTHQGLSSPV TKSFNRGEC*
```

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one," The use of the term "or" in the claims is used to mean "and/or" unless explicitly indicated to refer to alternatives only or the alternatives are mutually exclusive, although the disclosure supports a definition that refers to only alternatives and "and/or," Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic (s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An isolated humanized monoclonal antibody or binding fragment thereof that specifically binds the Plexin-Semaphorin-Integrin (PSI) domain of human RON, comprising an immunoglobulin heavy chain variable region and an immunoglobulin light chain variable region, wherein the immunoglobulin heavy chain variable region comprises complementarity determining region (CDR) sequences as set forth in SEQ ID NO: 7, SEQ ID NO: 8, and SEQ ID NO: 9, and the immunoglobulin light chain variable region comprises CDR sequences as set forth in SEQ ID NO: 10, SEQ ID NO: 11, and SEQ ID NO: 12.

2. The antibody or binding fragment thereof of claim 1, wherein the monoclonal antibody or binding fragment thereof is combined with a cytotoxic agent, such that the antibody targets a RON protein on a cell and the RON-monoclonal antibody and the cytotoxic agent are internalized into the cell.

3. The antibody or binding fragment thereof of claim 1, wherein the antibody or binding fragment thereof is a fusion protein with a cytotoxic protein.

4. The antibody or binding fragment thereof of claim 1, further comprising a cytotoxic or chemotherapeutic agent that is conjugated to the antibody or binding fragment thereof.

5. The antibody or binding fragment thereof of claim 1, wherein the heavy chain has an amino acid sequence as shown in SEQ ID NO: 15 and the light chain has an amino acid sequence as shown in SEQ ID NO: 16.

6. The antibody or binding fragment thereof of claim 1, wherein the immunoglobulin heavy chain CDR sequences are encoded by SEQ ID NOs: 1, 2, and 3, respectively.

7. The antibody of or binding fragment thereof claim 1, wherein the immunoglobulin light chain CDR sequences are encoded by SEQ ID NOs:4, 5, and 6, respectively.

8. The antibody or binding fragment thereof of claim 1, wherein the CDR sequences are interposed between human and humanized framework sequences wherein the framework sequence comprises at least one substitution at amino acid position 27, 30, 48, 67 or 78, wherein the amino acid numbering is based on Kabat.

* * * * *